United States Patent [19]
Howland

[11] Patent Number: 5,380,323
[45] Date of Patent: Jan. 10, 1995

[54] CLAMPS FOR SPINAL FIXATION SYSTEMS

[75] Inventor: Robert S. Howland, Seal Beach, Calif.

[73] Assignee: Advanced Spine Fixation Systems, Inc., Cypress, Calif.

[21] Appl. No.: 78,724

[22] Filed: Jun. 16, 1993

[51] Int. Cl.⁶ ............................................. A61F 5/00
[52] U.S. Cl. ...................... 606/61; 606/73; 623/17
[58] Field of Search ............... 606/60, 61, 72, 73; 623/17

[56] References Cited
U.S. PATENT DOCUMENTS

| | | | |
|---|---|---|---|
| 5,002,542 | 3/1991 | Frigg | 606/61 |
| 5,030,220 | 7/1991 | Howland | 606/61 |
| 5,053,034 | 10/1991 | Olerud | 606/61 |
| 5,129,900 | 7/1992 | Asher et al. | 606/73 |
| 5,190,543 | 5/1993 | Schläpfer | 606/61 |

OTHER PUBLICATIONS

Krag, et al., "Internal Fixator for Posterior Application", *Clinical Orthop.* 203, p. 81 (1986).

*Primary Examiner*—Stephen C. Pellegrino
*Assistant Examiner*—Sonya C. Harris
*Attorney, Agent, or Firm*—Christie, Parker & Hale

[57] ABSTRACT

A spinal fixation system. The spinal fixation system has a set of screw clamp assemblies adapted for attachment of a rod. The spinal fixation system comprises anchor screws and clamps. The anchor screws include a shoulder width "y" that varies within the anchor screws in the set to seat a clamp at a desired distance above the plane of the spine into which the anchor screws are implanted. The clamps include an arm length "x" that varies within the clamps in the set to attach the rod at a desired distance from the clamp seat site and apertures for receiving the rod within the clamps, wherein the apertures are set at an angle "a" from a plane perpendicular to the long axis of the anchor screw when a clamp is seated on the anchor screw that varies within the clamps in the set.

20 Claims, 9 Drawing Sheets

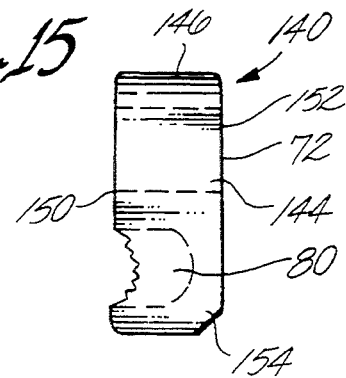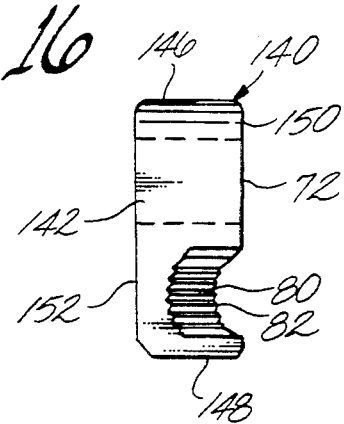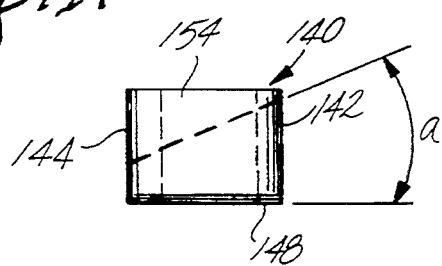

CLAMPS FOR SPINAL FIXATION SYSTEMS

FIELD OF THE INVENTION

This invention relates to an implantable spinal fixation device for the surgical treatment of spinal disorders which may require correction, stabilization, adjustment or fixation of the spinal column, in particular this invention relates to clamps used in such surgical treatment.

BACKGROUND OF THE INVENTION

Various types of spinal column disorders are known and include scoliosis (abnormal curvature of the spine), kyphosis (backward curvature of the spine), spondylolisthesis (forward displacement of a lumbar vertebra), and other disorders such as ruptured or slipped discs, broken or fractured vertebrae, and the like. Patients who suffer from such conditions usually experience extreme and debilitating pain. In severe cases treatments for these conditions have used a technique known as fusion with spinal fixation which results in the surgical/-mechanical immobilization of areas of the spine and the eventual fusion of the vertebrae in the regions treated. In less severe cases treatment comprises decompression of the affected nerve and fusion of the vertebrae involved.

Spinal fixation procedures use the implantation of screws into the vertebra in the affected region of the spine. Clamps are attached to the screws. The clamps are, in turn, clamped onto a rod which spans adjacent vertebra and thus fixes the vertebrae relative to each adjacent vertebrae. Since there is a large individual variation in the curvature of the spine and relative positioning of anchor screws in the vertebrae, the rods have to be bent to correctly "meet up" with the clamps.

Bending of the rod adjusts for differences: in the location of the clamps once they are positioned on the screws; in left-to-right displacements; and in the elevation of the clamp, which is often angled, relative to the plane of the spine (the anchor screws are often placed at different angles in the vertebrae to ensure they are placed in the safest part of the vertebrae). As a result of these differences rod receiving apertures of the clamps do not align. Therefore, the rod must be bent so that it can align with the rod receiving apertures of the clamps even apart from bending needed to induce normal spine curvature.

Bending of the rods is normally performed once the screws and clamps are in place in the vertebrae. Therefore, this must take place during the surgical procedure, while the patient remains under anesthetic. The bending of the rods, therefore, prolongs and, as a result, may adversely affect the outcome of the surgery. Also, bending the rods requires great skill on the part of the surgeon and requires extensive manipulations of the rods. These manipulations may lead to an increase in the possibility of contaminating the rod and, thereby, increasing post-surgical infection. Also, bending of the rods introduces the possibility of developing stress fractures in the rods and, because the rods are bent during surgery, the structural integrity of the bent rods can not be checked.

Adjustable screws and clamps have been used in an attempt to eliminate the amount of rod adjustment required to properly clamp the rods in place. One such device incorporates an articulated clamp allowing rotation of the rod relative to the plane of the spine. Another device, described in U.S. Pat. No. 5,053,034 to Olerud, uses a "spinal joint" which allows rotation of the rod relative to the plane of the spine. These devices do not allow the clamps to be elevated relative to the plane of the spine nor do they allow for right-to-left adjustments. Also, the adjustable elements introduce the possibility of the clamps loosening during use.

Another device is described in U.S. Pat. No. 5,002,542 to Frigg and a device of a similar function is described in U.S. Pat. No. 5,129,900 to Asher et al. These devices allow adjustment in the distance of the rod from the screw, i.e. right-to-left adjustment by use of a slot adjustment. However, these devices do not allow for adjustment of the height or angle of the clamps. Again the adjustable elements of these designs introduces the possibility of the elements loosening after implantation.

Another adjustable design is described in U.S. Pat. No. 5,030,220 to Howland and uses a spacer to adjust the height of the clamp above the plane of the spine. However, this design does not allow for right-to-left adjustment or adjustment of the angle of the clamp. Also, the use of a spacer requires the assembly of a number of small components during surgery. This can be difficult under surgical conditions with gloved hands.

It is desirable that a fixation device be provided which facilitates connection of the rod to the clamps. It is further desirable that such a device does not require manipulation of multiple small components. It is also desirable that such a device has only a few moveable parts, which could loosen after implantation.

SUMMARY OF THE INVENTION

A spinal fixation system is described. The spinal fixation system has a set of screw clamp assemblies adapted for attachment of a rod. The clamps allow the selection of clamps and anchor screws that minimize the need to bend the rod to conform to the curvature of or site of attachment in the spine of the patient. The spinal fixation system comprises anchor screws and clamps.

The anchor screws include a shoulder width "y" that varies within the anchor screws in the set. The different shoulder widths allow a clamp to be seated at a desired distance above the plane of the spine into which the anchor screws are implanted.

The clamps include an arm length "x" that varies within the clamps in the set. The different arm lengths allow the clamp to be attached to the rod at a desired distance from the clamp seat site. The clamps also include apertures for receiving the rod within the clamps wherein the apertures are set at an angle "a" from a plane perpendicular to the long axis of the anchor screw when a clamp is seated on the anchor screw that varies within the clamps in the set. The different aperture angles allow the rod to be maintained in a plane approximately parallel to the plane of the spine.

BRIEF DESCRIPTION OF THE DRAWINGS

Features, aspects and advantages of the invention will be more fully understood when considered with respect to the following detailed description, appended claims and accompanying drawings where:

FIG. 15 is a side view taken along the line 15—15 of FIG. 14;

FIG. 16 is a side view taken along the line 16—16 of FIG. 14;

FIG. 17 is an end view taken along the line 17—17 of FIG. 14;

DETAILED DESCRIPTION

Figure 1:
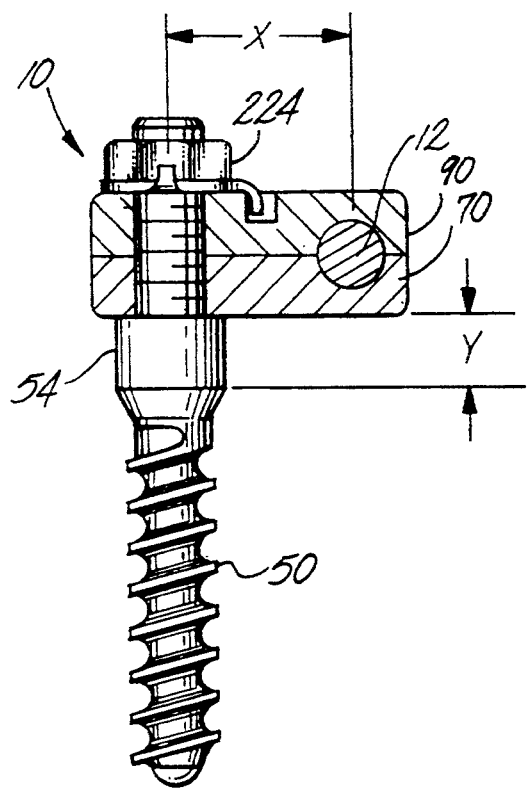
FIG. 1 is a side view, partly in section illustrating the mating fit of the upper- and lower-half clamps.
Figure 2:
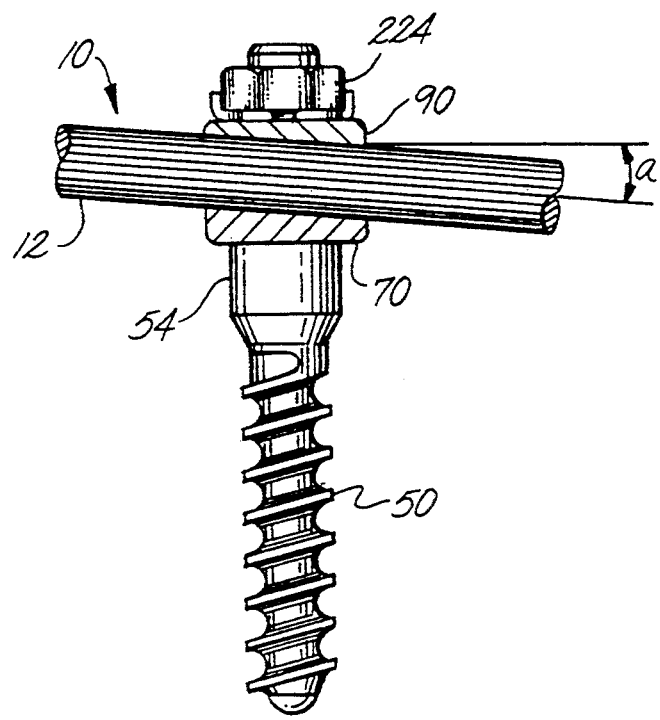
FIG. 2 is a front view, partly in section, on the same side as the rod receiving aperture, illustrating the mating fit of the upper- and lower-half clamps.

The present invention relates to a fixation device system, comprising clamp and screw assemblies 10 which are available in a set of components that include preset adjustments. The adjustments (see FIGS. 1 and 2) include an adjustment for the distance "x" of the centerline of rod 12 from the centerline of screw 50, an adjustment for the angle "a" of the rod relative to the plane of the spine and an adjustment for the height "y" of the rod above the plane of the spine. The preset adjustments are supplied as incremental adjustments. In one embodiment of the present invention, a set of upper- and lower-clamps 90 and 70, respectively, are supplied wherein "x" is varied from about 6 to about 12 mm, in increments of about 1 mm, and "a" varies from about $-14°$ to about $+14°$ (where 0° is defined as perpendicular to the longitudinal plane of anchor screw 50) in increments of about 7°. The distance "y" is varied from about 0.25 to about 8.25 mm in about 2 mm increments. Therefore, there are three areas of adjustment: on the anchor screw; on the clamp arms; and on the rod receiving aperture. Each of these elements can be combined with straight (see FIGS. 7–10), right- (see FIG. 11) or left-hand offset clamps (see FIG. 12). Likewise all the clamps can be combined with either a sleeve nut (see FIGS. 4, 10 and 13) or nut and lock washer (see FIGS. 1, 2, 18 and 22) attachment mechanism. Different aspects of the invention are described below. For simplicity, only one aspect or embodiment of the present invention is shown for each drawing, however, it is understood that each of these aspects can be interchanged and combined to meet the needs of a particular situation or as otherwise needed or desired.

Figure 3:
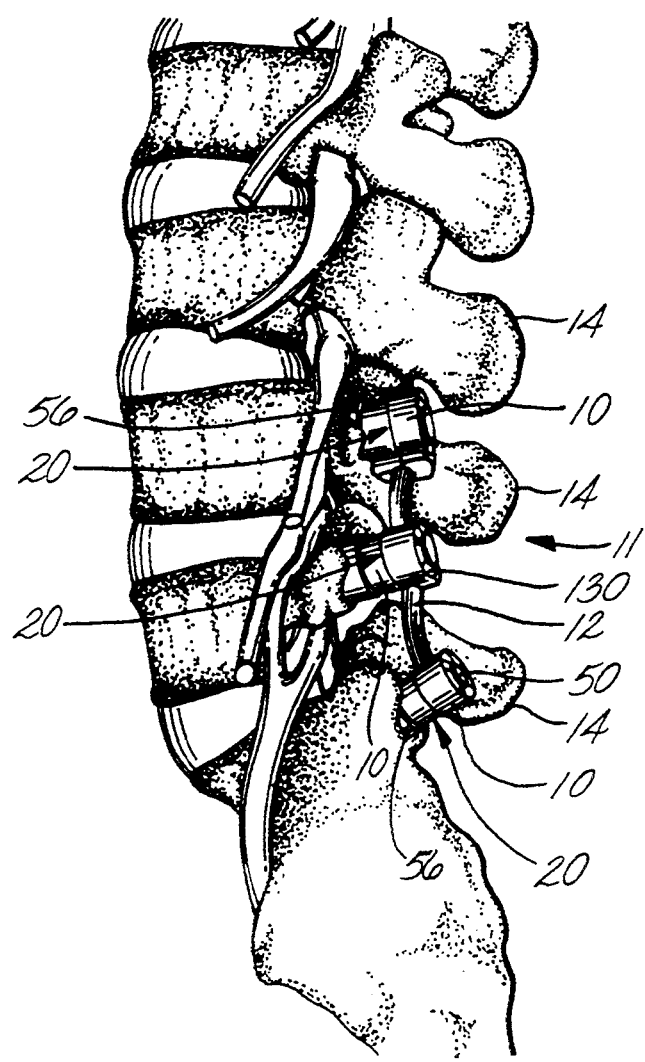
FIG. 3 is a diagrammatic lateral view of one embodiment of a spinal fixation system of the present invention, installed in a portion of the spinal column.
Figure 4:
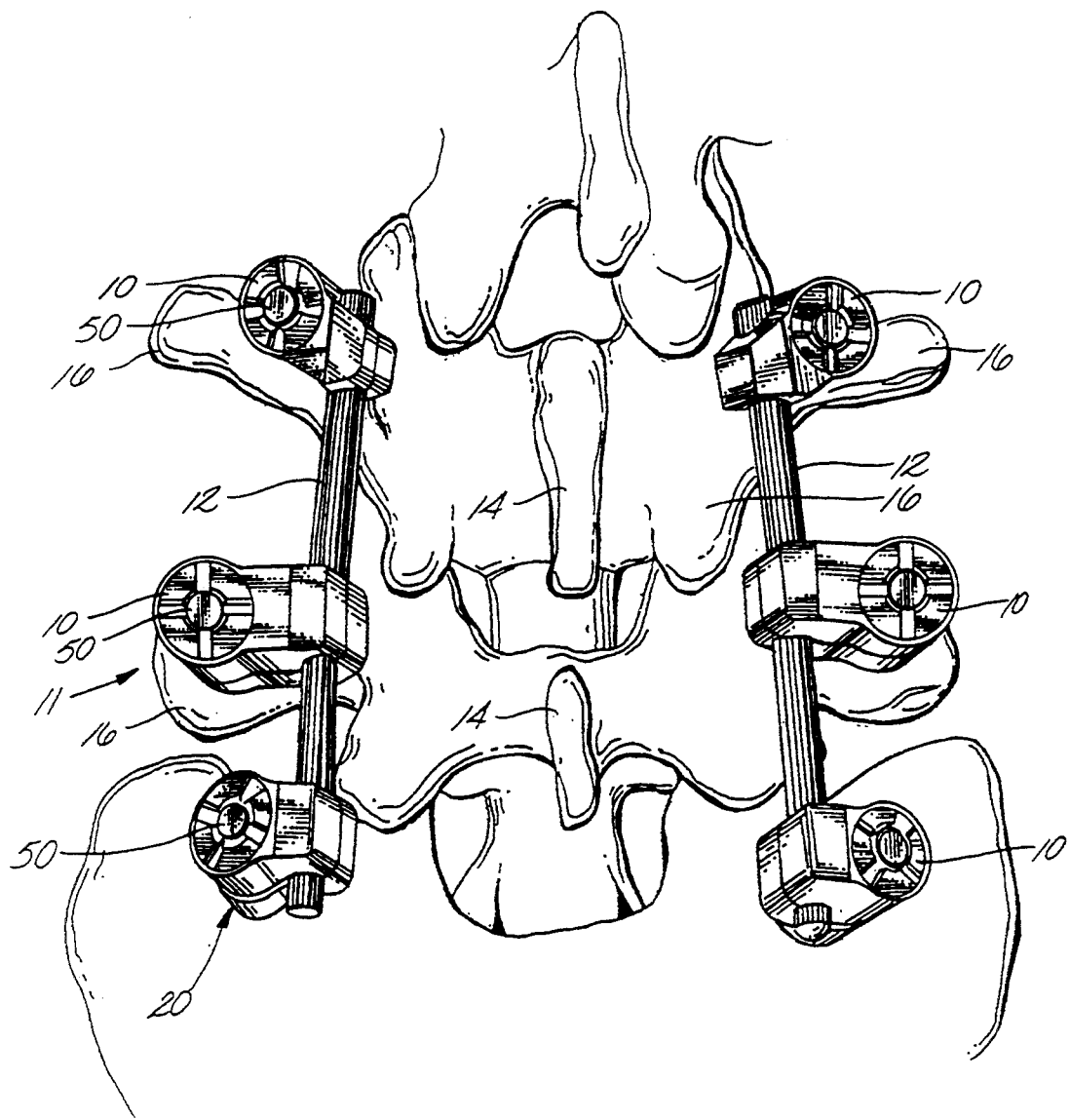
FIG. 4 is a diagrammatic posterior view of the spinal support fixation system illustrated in FIG. 3.

As illustrated in FIGS. 3 and 4, spinal support system 11, is attached to S1, L5 and L4 vertebra to stabilize the spine in this region (although other attachment sites and corrections are also possible). The spinal fixation system includes a plurality of screw-clamp assemblies 10, each of which is preferably located between spinous process 14 and associated transverse process 16 on each side of the spinous process and in the posterior portion of the spinal column. As shown, one screw-clamp assembly is placed in each side of each vertebra, and each of the screw-clamp assemblies supports and firmly holds a rod 12.

The screw-clamp assembly is attached to the pedicle by an anchor screw 50 (see FIGS. 5 and 6) to which is attached a clamp assembly 20. In accordance with a preferred embodiment of the invention, the clamp assembly is removable from the anchor screw and is preferably formed of a lower-half 70 and an upper-half 90, as shown in FIGS. 7–12 and 14–21. The upper- and lower-half clamps mate and firmly grip and purchase on rod 12. The rod is serrated, as are the mating apertures of the upper- and lower-half clamps. The upper- and lower-half clamps are attached to the anchor screw by sleeve nut 130, which is shown in detail in FIG. 13.

In FIGS. 3 and 4 the clamp assemblies are shown assembled medially, but can be reversed and assembled with the support rod laterally.

Figure 5:
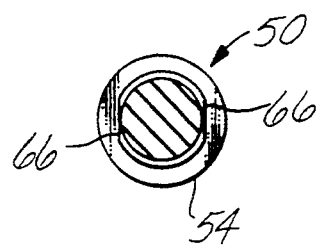
FIG. 5 is a top view, in section, of an anchor screw taken along the line 5—5 of FIG. 6.
Figure 6:
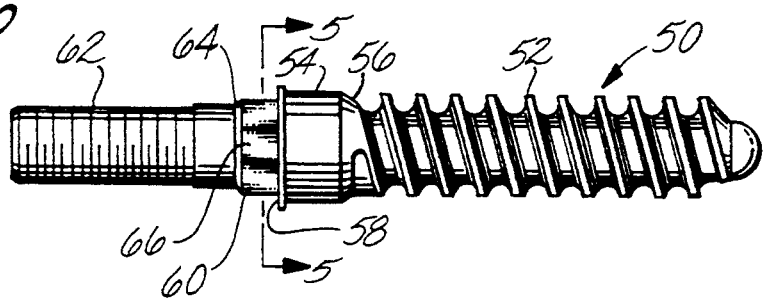
FIG. 6 is a side view of a anchor screw in accordance with the present invention.

Referring now to FIGS. 5 and 6, anchor screw 50 includes a lower, course-threaded end 52 for placement and attachment of the screw-clamp assembly into the bony structure of the vertebrae of the spine. The preferred location is determined by the surgeon and is usually through the pedicle, although other regions, such as the sacral region, may be used. The screw may be inserted directly into the vertebrae or they may be placed in predrilled openings, dimensioned to receive the threads of the anchor screw firmly in an appropriate support structure of the spine. The configuration of the anchor screw threads is well known in the art and is that which is normally used for screw members intended to be implanted in bone structures. The lower threaded end of the anchor screw terminates in a shoulder 54 that is tapered on side 56 which abuts the lower threaded end of the anchor screw. The other side of the shoulder has a flat face 58. The provision of the shoulder permits the clamp assembly to be positioned close to the vertebra into which the anchor screw is positioned without the clamp assembly resting on the vertebra. The shoulder also inhibits anchor screw breakage and pullout of the anchor screw from the vertebra after installation, which could result from mechanical stresses placed on the anchor screw if the clamp assembly were resting on the vertebra.

The length "y" of shoulder 54 (FIG. 1) is varied within a set of anchor screws to allow adjustment of the height of the clamps above the plane of the spine. In one embodiment of the present invention, the anchor screws are available with the length of the shoulder preset at lengths of from about 0.25 to about 8.25 mm, in increments of 2 mm. Therefore, 5 different anchor screws are supplied to meet the needs of the surgeon. This allows the surgeon to select an anchor screw, with the height required to minimize the bending of the rod required to align with the clamps attached to adjacent vertebrae.

Immediately adjacent the flat face of the shoulder is a generally-cylindrical clamp location section 60, whose diameter is less than that of the shoulder but greater than the major diameter of an adjacent upper threaded end 62. A fillet radius 64 is located at the junction of the clamp location section and the upper threaded end. The generally-cylindrical clamp seat section includes two flat sections 66, located 180° from each other, which operate as locators for the lower-half clamp to prevent rotation of the lower-half clamp relative to the anchor screw when the anchor screw and clamp are assembled.

The anchor screw, as well as the other components of the spinal fixation system, is preferably made of 316 LVM stainless steel, which is electro-polished and passivated to resist corrosion by body fluids. The anchor screws come in various lengths and diameters to accommodate the need of the surgeon in attaching the spinal fixation system.

Figure 7:
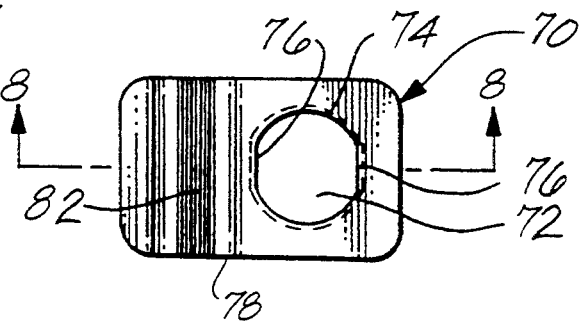
FIG. 7 is a top view of the upper-side of a lower-clamp assembly in accordance with the present invention.
Figure 8:
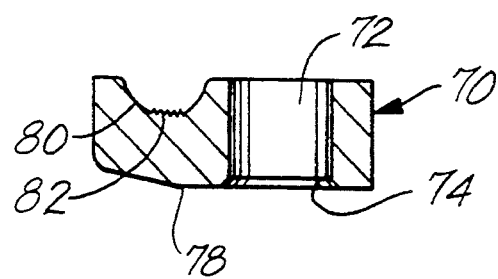
FIG. 8 is a side view, partly in section and partly in elevation, taken along the line 8—8 of FIG. 7.

FIGS. 7 and 8 illustrate the structure of lower-half clamp 70 of the clamp assembly. The lower-half clamp is provided with an aperture 72 for receipt on clamp location section 60 of anchor screw 50. A chamfer line 74 is located on the lower surface of the lower-half clamp. The lower-half clamp is assembled such that its bottom surface is seated on face 58. The aperture is provided with opposing flat surfaces 76, which mate with flat surfaces 66 on the clamp location section of the anchor screw. The axial length of the lower-half clamp is approximately that of the axial length of the clamp location section. The lower-half clamp also includes an arm 78 which forms a rod-receiving aperture 80, laterally of aperture 72. The aperture is serrated along its length, as indicated at 82, for mating with and gripping the serrated rod.

Figure 9:
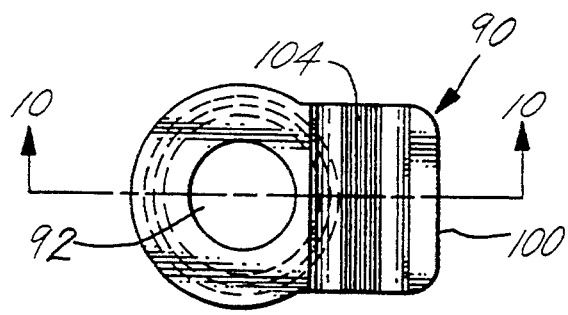
FIG. 9 is a bottom view of the underside of one embodiment of an upper-clamp assembly in accordance with the present invention.
Figure 10:
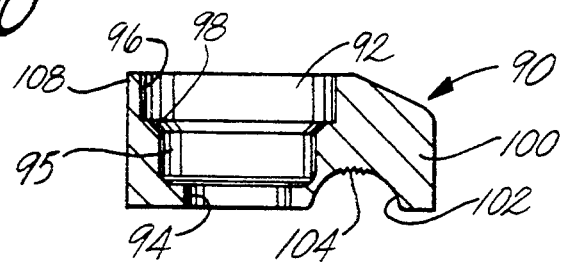
FIG. 10 is a side view, partly in section and partly in elevation, taken along line 10—10 of FIG. 9.

FIGS. 9 and 10 illustrate an upper-half clamp 90, which is provided with an aperture 92 for receipt on upper threaded end 62 of anchor screw 50. The axial length of the upper-half clamp is the same as that of upper threaded end 62 of the anchor screw so that, when assembled, none of the threaded portion extends beyond upper-half clamp 90.

In one embodiment of the present invention, the internal diameter of the upper-half clamp is stepped. A lower section 94 has a diameter such that, when placed on the anchor screw, the upper-half clamp will fit securely against threaded section 62 of the anchor screw. An intermediate section 95, which abuts the lower section, has an intermediate diameter which is greater than the diameter of the lower section. Adjacent the intermediate section is an upper section 96, which has a diameter larger than that of the intermediate section. The intermediate and upper sections are separated by a chamfer line 98. When assembled, the intermediate and upper sections accommodate a sleeve nut 130 (see FIG. 13).

The upper-half clamp also includes an arm 100 which forms an aperture 102 laterally of aperture 92. The aperture is serrated along its length, as indicated at 104, for mating and gripping the serrated rod. When assembled, the serrated surfaces of the upper- and lower-half clamps are in facing relation to each other and mate with and firmly grip the serrated rod.

The upper- and lower-half clamp can be varied so that the distance "x" from the attachment site of the anchor screw to the aperture (FIG. 1) can be varied. In a preferred embodiment the upper- and lower-half clamps within a set of clamps are supplied with arm lengths "x" of from about 6 to about 12 mm, in increments of 1 mm. Therefore, 7 upper- and 7 lower-half clamps with different arm lengths are available to meet the needs of the surgeon. The surgeon can, therefore, choose the appropriate clamp to minimize bending of the rod.

Figure 11:
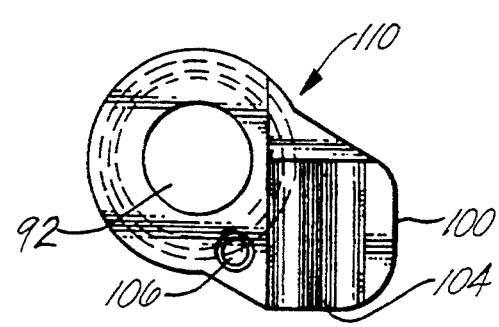
FIG. 11 is a bottom view of the underside of one embodiment of a right-handed offset upper-clamp assembly in accordance with the present invention.
Figure 12:
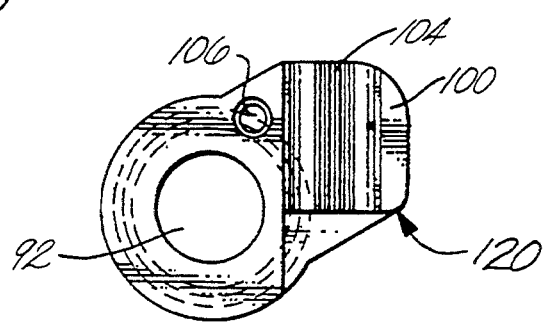
FIG. 12 is a bottom view of the underside of one embodiment of a left-handed offset upper-clamp assembly in accordance with the present invention.

FIGS. 11–12 illustrate alternative embodiments for the clamp assemblies of the present invention. Illustrated are upper-half clamps 110 and 120 which are right-hand offset or left-hand offset, respectively. Not illustrated are matching right- and left-handed offset lower-half clamps, although it will be understood by one skilled in the art that such lower-half clamps would be structured to mate with the respective upper-half clamps described. Since these upper-half clamps have parts that are essentially the same as parts previously described (see FIGS. 9 and 10), the same reference numerals are used for the same parts. The positioning of a right-hand offset clamp is shown in FIG. 4, attached to the L4 vertebra. These offset half clamps are convenient for avoiding contact with facets of the superior vertebrae, where the straight half clamps (see FIGS. 7–10) would interfere with the surrounding bone of the facets. In one embodiment of the present invention the right- and left-hand offset upper-half clamps include a pin-clearance hole 106 which mates with a pin located on the lower-half clamp, not shown. The pin and clearance-hole prevent rotation of the upper- and lower-half clamps, relative to each other when they are assembled. When assembled, the lower- and upper-half clamps are placed on the anchor screw, as described above.

These offset clamps can also be supplied in sets with a preset incremental adjustable format as described above.

Figure 13:
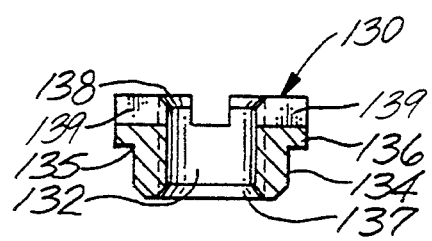
FIG. 13 is a side view, partly in section and partly in elevation, of a sleeve nut.
Figure 14:
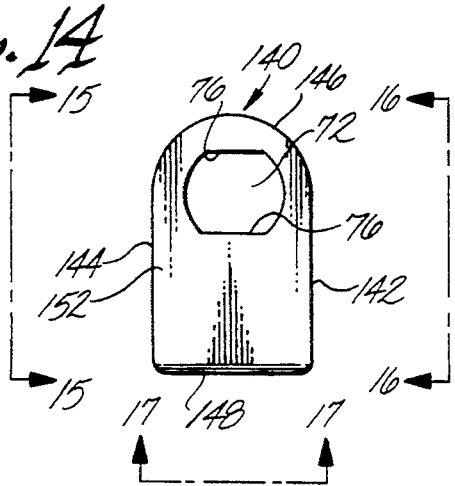
FIG. 14 is a plan view of the bottom surface of an angled lower-clamp.
Figure 18:
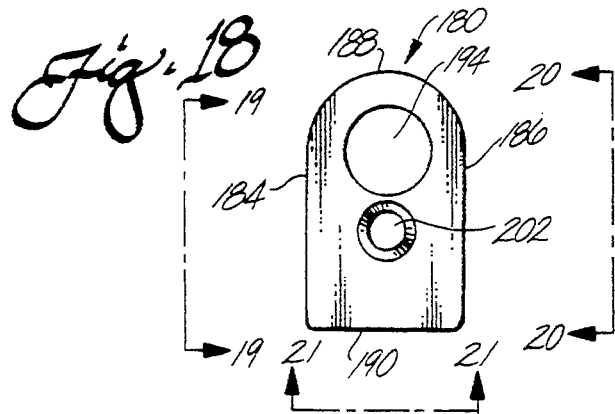
FIG. 18 is a plan view of the top surface of one embodiment of an angled upper-clamp.
Figure 19:
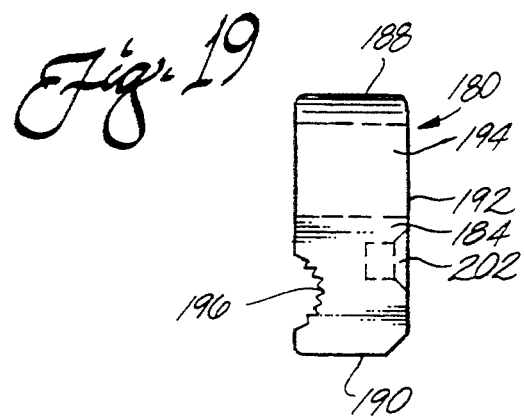
FIG. 19 is a side view taken along line 19—19 of FIG. 18.
Figure 20:
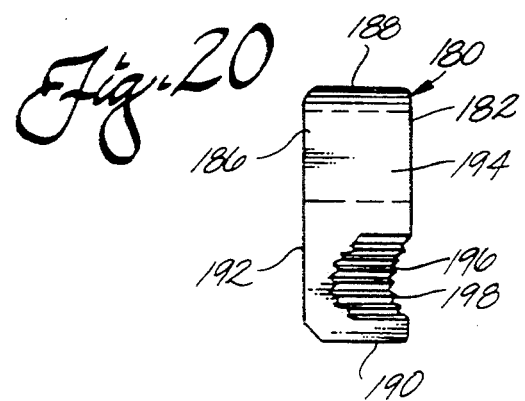
FIG. 20 is a side view taken along line 20—20 of FIG. 18.
Figure 21:
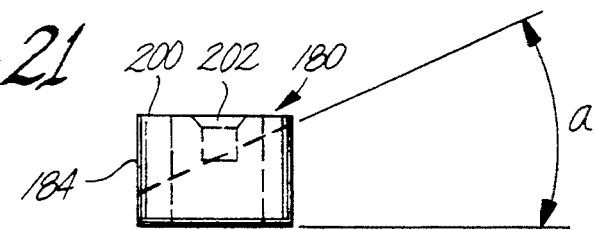
FIG. 21 is an end view taken along line 21—21 of FIG. 18.
Figure 22:
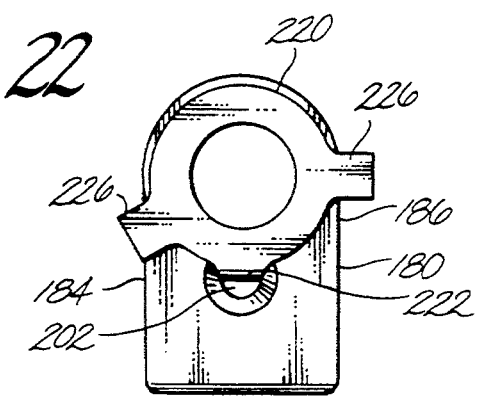
FIG. 22 is a view similar to FIG. 18 but illustrating an angled upper-clamp on which a lock washer is secured.

In one embodiment of the present invention, a sleeve nut 130 is used to hold the lower- and upper-half clamps in place on anchor screw shoulder 54 and to ensure a firm grip on the rod. The sleeve nut is illustrated in FIG. 13. Sleeve nut 130 has an aperture 132, which is threaded so that it mates with threaded portion 62 of the anchor screw.

The exterior of the sleeve nut is of different diameters. At lower end 134 of the sleeve nut, the diameter of sleeve nut is at its smallest and is sized such that the sleeve nut will fit into stepped region 94 and 95 of the upper-half clamp. At the upper end 136 of the sleeve nut, and adjacent small-diameter portion 134, is a large-diameter portion of the sleeve nut. A fillet radius 135 is located at the juncture of the small- and large-diameter portion of the sleeve nut. The large-diameter portion is sized so that it will fit into stepped region 96 of the upper-half clamp, thus holding the upper-half clamp and the lower-half clamp securely in place when the sleeve nut is screwed onto the anchor screw. The stepped interior of the upper-half clamp allows a distribution of the force conferred by the sleeve nut on the upper-half clamp over a larger area. A chamfer line 137 is locate at the bottom of the sleeve nut. When the sleeve nut is tightened onto the anchor screw, chamfer line 137 will not engage fillet radius 64 of the anchor screw.

Top face 138 of the sleeve nut includes four radial notches 139, placed at equal distances from each other. The notches align with prongs of a driver, not shown. In one embodiment of the present invention the driver is attached to a torque wrench for tightening the sleeve nut into the upper-half clamp to ensure that the correct pressure is applied. Preferably the sleeve nut is tightened to about 100 in. lb of torque. In a preferred embodiment, the driver comprises a mechanism for holding the sleeve nut so that the surgeon can more easily attach the sleeve nut to the anchor screw.

In use, the lower-half clamp is assembled over an anchor screw, and then, after the rod is in position, the upper-half clamp is installed. The sleeve nut is then threaded on the upper threaded-end portion of the anchor screw and tightened down, using the driver. The prongs of the driver are mated with the notches of the sleeve nut and the driver is then used to tighten the sleeve nut into the upper-half clamp. The sleeve nut, when tightened down, is completely contained within aperture 92, leaving exposed a small portion of the upper edge of wall 108 of the upper-half clamp.

After the sleeve nut is in place, the exposed portion of wall 108 (see FIG. 10) is crimped at one point along its periphery corresponding to one of the radial notches. The crimp ensures that the sleeve nut is firmly locked in place and that undesired rotation of the sleeve nut is inhibited.

In the event that some adjustment, and hence removal of the sleeve nut is necessary, the crimp is easily overcome by using the driver to remove the sleeve nut, and the sleeve nut is unscrewed to release the upper- and lower-half clamps. After any required adjustment has been made, the screw-and-clamp assembly is secured in place, as described above.

FIGS. 14-17 illustrate an angled lower-clamp 140. Since the angled lower-half clamps have parts that are essentially the same as parts of those previously described in FIGS. 7 and 8, the same reference numerals are used for the same parts. The angled lower-clamp includes an unthreaded aperture 72. The aperture has internal flat sections 76 which mate with flat sections 66 on the anchor screw preventing rotation of the lower-clamp relative to the anchor screw when the fixation system is assembled. The lower-clamp includes side faces 142 and 144, which are generally flat, a curved rear face 146, a front face 148 and top and bottom faces 150 and 152, respectively.

Located in top face 150 and between aperture 72 and front face 148 is a rod-receiving aperture 80 on which a rod is received. The aperture is preferably serrated, as indicated at 82, the serrations extending axially from one side face to the other to mate with serrations on the rod, which is described in detail below.

Bottom face 152 of the lower-clamp is generally flat and abuts shoulder 54 of the anchor screw when assembled on the anchor screw, i.e., this face is oriented in a plane which is perpendicular to the long axis of the anchor screw. Top face 150 of the lower-left clamp is generally parallel to bottom face 152. Aperture 80 is oriented in a plane which is at an angle to bottom face 152 and top face 150. Accordingly, the axial dimension from the bottom of aperture 80 to the bottom face along side face 142 is less than the axial dimension from the bottom of aperture 80 to the bottom face along side face 144.

This geometry places the aperture at an inclined orientation, which is angularly oriented with respect to the long axis of the anchor screw at an angle "a". Angle "a" (FIG. 2) is preset within a set of clamps at incremental variations between about −14° to about +14° in increments of 7°. Therefore, 5 angled lower-clamps are available to meet the needs of the surgeon.

An angled upper-clamp 180, of one embodiment of the present invention, is illustrated in FIGS. 18–21. The upper-clamp includes a bottom face 182 adapted to be positioned in facing relation with top face 150 of the lower-clamp, side faces 184 and 186, a curved rear face 188 and a front face 190 and a top face 192. The upper-clamp includes an unthreaded generally circular aperture 194 which aligns with the aperture of the lower-clamp and when assembled is placed over end 62 of the anchor screw. There are no interior flats in aperture 194.

Located in bottom face 182 and between aperture 194 and front face 190 is aperture 196 on which a rod is received for clamping. Aperture 196 is preferably serrated, as indicated at 198, the serrations extending axially from one side face to the other to mate with serrations on the rods when the fixation device is assembled together.

Top face 192 of the upper-clamp is generally flat and is oriented in a plane which is perpendicular to the long axis of the anchor screw and generally parallel to lower or bottom face 152 of the lower-clamp. Bottom face 182 of the upper-left clamp is oriented so it is generally parallel to top face 192. Aperture 196 is in an angular orientation for a mating fit with aperture 80 of the lower-clamp. Accordingly, the axial dimension from the bottom of aperture 196 to the top face along side face 186 is less than the axial dimension from the bottom of aperture 196 to the top face along side face 184.

This geometry, in effect, places aperture 196 in an inclined orientation which is angularly oriented with respect to the long axis of the anchor screw at an angle "a". Angle "a" is preset within a set of clamps at incremental variations between about −14° to about +14° in increments of 7°. Therefore, 5 angled lower-clamps are available to meet the needs of the surgeon.

Typically, the rods made of the material already described, are about 4.5 mm in diameter and may vary in length from about 25 mm to at least about 100 mm as required for the fixation procedure being performed. The outer surface of the rod is serrated along its length, having for example 28 teeth and the serrations match those on the apertures of the clamps.

Unlike the lower-clamp, upper-clamp 180 in this embodiment of the present invention has provided in top face 192 a blind aperture 202, the latter located between aperture 194 and inclined portion 200 of the top face. In one embodiment of the present invention, described in detail below, a locking assembly comprises a locking washer 220 wherein a locking tang 222 of a lock washer is received in aperture 202. As illustrated on an angled upper-clamp, in FIG. 22, lock washer 220 is a separate item assembled between upper-clamp 180 and nut 224 (see FIGS. 1, 2 and 22).

In the assembly procedure one tang 222 of the washer is deformed into the blind aperture, nut 224 is threaded over the distal end of the anchor screw and tightened and remaining tangs 226 are deformed to grip the sides of the nut. Tang 222 effectively attaches lock washer 220 to the upper-clamp. When tangs 224 are deformed upwardly they lock the nut in place and prevent it from loosening after installation.

The sets of spinal clamp screw assemblies of the present invention allow for three areas of adjustment: on the anchor screw "y"; on the clamp arms "x"; and on the rod receiving aperture "a." In a preferred embodiment the clamps and screws are supplied with 5 different anchor screw length adjustments, 7 different clamp arm adjustments and 5 different rod receiving aperture adjustments. Therefore, in this embodiment there are a total of 35 individual clamps which incorporate each of the different incremental adjustment of the clamp arm and rod receiving aperture. Each of these 35 clamp can be used with the 5 different incremental adjustments on the anchor screw to give the surgeon a total of 175 possible combinations.

The present invention is not limited to the specific designs shown. Therefore, the present invention is not intended to be limited to the working embodiments described above. The scope of the invention is defined in the following claims.

What is claimed is:

1. A spinal fixation system having a set of screw clamp assemblies adapted for attachment of a rod comprising:

anchor screws, wherein each anchor screw within the set includes a shoulder width "y", wherein the shoulder width "y" is varied, at fixed preset increments, from one anchor screw in the set to the next to provide a set of anchor screws from which a desired shoulder width can be chosen to seat a clamp at a desired distance above the plane of the spine into which the anchor screws are implanted;

clamps adapted to be seated on the anchor screws, wherein each clamp includes an arm length "x", wherein the arm length is varied at fixed preset increments from one clamp in the set to the next to provide a set of clamps from which a desired arm length can be chosen to attach the rod at a desired distance from the clamp seat site; and each of the clamps comprised of upper-half clamps and lower-half clamps which matingly form an aperture for receiving the rod within the clamps, wherein each of the apertures of the clamps are adapted to hold a rod at a fixed preset angle "a" from a plane perpendicular to a longitudinal axis of the anchor screw when a clamp is seated on the anchor screw wherein angle "a" is varied from one clamp in the set to the next to provide a set of clamps from which a desired angle can be chosen.

2. A spinal fixation system as recited in claim 1 wherein "a" is varied in preset increments between about $-14°$ and about $+14°$.

3. A spinal fixation system as recited in claim 2 wherein "a" varies in increments of about 7°.

4. A spinal fixation system as recited in claim 1 wherein "x" varies between about 6 mm and about 12 mm.

5. A spinal fixation system as recited in claim 4 wherein "x" varies in increments of about 1 mm.

6. A spinal fixation system as recited in claim 1 wherein "y" varies between about 0.25 mm and about 8.25 mm.

7. A spinal fixation system as recited in claim 6 wherein "y" varies in increments of about 2 min.

8. A spinal fixation system comprising:

an assortment of anchor screws, each anchor screw comprising:

a first end for fastening the anchor screw to a vertebra;

a second end opposite the first end;

a shoulder located between the first and second ends and having a lower face, facing the vertebra and an upper face opposite the lower face, the shoulder having a shoulder height between the upper and lower faces wherein the assortment includes anchor screws having various shoulder heights;

an assortment of clamps for connecting a spine rod to the anchor screws, each clamp comprising:

an upper-half clamp and a lower-half clamp;

the upper-half clamp and lower-half clamp having an aperture for fastening to the anchor screw, the lower-half clamp engaging the upper face of the shoulder;

the upper-half clamp and the lower-half clamp include a pair of facing channels, one of the pair being defined by the upper-half clamp and the other of the pair being defined by the lower-half clamp for receiving a spine rod at a particular rod angle from a plane perpendicular to a longitudinal axis of the vertebra wherein the assortment includes channels which hold the rod at different angles from a plane perpendicular to a longitudinal axis of the vertebra; and means for clamping the spine rod within the facing channels wherein the clamps in the assortment have various different distances from the anchor screw to the facing channels; and means for fastening the clamps to the anchor screws.

9. A spinal fixation system as recited in claim 8 wherein the rod angles vary from about $-14°$ to about $14°$.

10. A spinal fixation system as recited in claim 9 wherein the rod angles vary in increments of about 7°.

11. A spinal fixation system as recited in claim 8 wherein the rod spacing widths vary from about 6 mm to about 12 mm.

12. A spinal fixation system as recited in claim 11 wherein the rod spacing widths vary in increments of about 1 mm.

13. A spinal fixation system as recited in claim 8 wherein the shoulder heights vary from about 0.25 to about 8.25 mm.

14. A spinal fixation system as recited in claim 13 wherein the shoulder heights vary in increments of about 2 mm.

15. A spinal fixation system as recited in claim 8 wherein the second end of the anchor screw further comprises an external thread and the means for clamping the spine rod within the channels of a pair of half clamps comprises a nut threaded to the second end of the anchor screw, the nut for pressing the half clamps together around the spine rod.

16. A spinal fixation system as recited in claim 15 wherein the rod angles vary from about $-14°$ to about $+14°$, the rod spacing widths vary from about 6 mm to about 12 mm and the shoulder heights vary from about 0.25 mm to about 8.25 mm.

17. A spinal fixation system as recited in claim 16 wherein the rod spacing widths vary in increments of about 1 mm, the rod angles vary in increments of about 7° and the shoulder heights vary in increments of about 2 mm.

18. A spinal fixation system comprising:

a set of anchor screws, wherein each anchor screw within the set includes a shoulder width "y", wherein the shoulder width "y" is varied, at fixed preset increments, from one anchor screw in the set to the next to provide a set of anchor screws from which a desired shoulder width can be chosen to seat a clamp at a desired distance above the plane of the spine into which the anchor screws are implanted;

clamps for seating on the anchor screw, wherein the clamps include facing channels for receiving a rod; and means for attaching the clamp to the anchor screw.

19. A spinal fixation system comprising:

anchor screws;

a set of clamps adapted to be seated on the anchor screws, wherein each clamp includes an arm length "x" wherein the arm length is varied at fixed preset increments from one clamp in the set to the next to provide a set of clamps from which a desired arm length can be chosen to attach the rod at a desired distance from the clamp seat site and wherein the clamps include facing channels for receiving a rod; and means for attaching the clamp to the anchor screw.

20. A spinal fixation system comprising:

anchor screws;

a set of clamps wherein each of the clamps comprised of upper-half clamps and lower-half clamps which matingly form an aperture for receiving a rod within the clamps, wherein each of the apertures of the clamps are adapted to hold a rod at a fixed preset angle "a" from a plane perpendicular to a longitudinal axis of the anchor screw when a clamp is seated on the anchor screw wherein angle "a" is varied from one clamp in the set to the next to provide a set of clamps from which a desired angle can be chosen; and means for attaching the clamps to the anchor screws.

* * * * *

UNITED STATES PATENT AND TRADEMARK OFFICE
CERTIFICATE OF CORRECTION

PATENT NO. : 5,380,323
DATED : January 10, 1995
INVENTOR(S) : Robert S. Howland

It is certified that error appears in the above-indentified patent and that said Letters Patent is hereby corrected as shown below:

Column 9, line 63, change "2 min." to -- 2 mm --.

Signed and Sealed this

Twenty-third Day of May, 1995

Attest:

BRUCE LEHMAN

Attesting Officer

Commissioner of Patents and Trademarks